US007008666B2

(12) United States Patent
Ahotupa et al.

(10) Patent No.: US 7,008,666 B2
(45) Date of Patent: Mar. 7, 2006

(54) METHOD OF INHIBITING OVERACTIVITY OF PHAGOCYTES OR LYMPHOCYTES IN AN INDIVIDUAL

(75) Inventors: Markku Ahotupa, Turku (FI); John Eriksson, Turku (FI); Lauri Kangas, Lieto (FI); Mikko Unkila, Littoinen (FI); Janne Komi, Turku (FI); Merja Perälä, Raisio (FI); Helena Korte, Turku (FI)

(73) Assignee: Hormos Nutraceutical Oy Ltd., Turku (FI)

( * ) Notice: Subject to any disclaimer, the term of this patent is extended or adjusted under 35 U.S.C. 154(b) by 0 days.

(21) Appl. No.: 09/991,971

(22) Filed: Nov. 26, 2001

(65) Prior Publication Data

US 2003/0100514 A1    May 29, 2003

(51) Int. Cl.
*A01N 43/20* (2006.01)
*A61K 31/34* (2006.01)
*A23L 1/30* (2006.01)
(52) U.S. Cl. ..................... 426/648; 435/7.71; 514/473
(58) Field of Classification Search ................ 514/473; 435/7.71; 426/648
See application file for complete search history.

(56) References Cited

U.S. PATENT DOCUMENTS 6,451,849 B1 *  9/2002  Ahotupa et al. ............ 514/473

FOREIGN PATENT DOCUMENTS

| EP | 0 906 761 A2 | 4/1999 |
| WO | WO 00/59946 A1 | 10/2000 |
| WO | WO 02/080702 A1 | 10/2002 |

OTHER PUBLICATIONS

Pool-Zobel et al, Carcinogenesis 21(6): 1247-52, 2000.*
The Merck manual, p. 420-421, 1999 edition.*
Morikawa et al, J. Pharm Pharmacol 44(10): 859-61, Oct. 1992.*
Yesilada et al, Cytokine 13(6): 359-364, Mar. 21, 2001.*
Yesilada, E. et al. (2001). "In Vitro Inhibitory Effects of *Daphne Oleoides* SSP. *Oleoides* on Inflammatory Cytokines and Activity-Guided Isolation of Active Constituents," *Cytokine* 13(6):359-364.
Cho, Jae Youl et al. (1999). "Immunomodulatory Effect of Arctigenin, a Lignan Compound, on Tumour Necrosis Factor-alpha and Nitric Oxide Production and Lymphocyte Proliferation," *J. Pharm. Pharmacol.* 51:1267-1273.
Yang, Li-Ming et al. (1996). "Synthesis and Anti-HIV Actvity of Dibenzylbutyrolactone Lignans," *Bioorganic & Medicinal Chem. Letts.* 6(8):941-944.
Cho, Min Kyung et al. (2002). "Potent Inhibition of Lipopolysaccharide-Inducible Nitric Oxide Synthase Expression by Dibenzylbutyrolactone Lignans Through Inhibition of I-κ Bα Phosphorylation and of p65 Nuclear Translocation in Macrophages," *Intl. Immunopharmacol.* 2:105-116.
Hirano, Toshihiko et al. (1994). "Natural Flavonoids and Lignans are Potent Cytostatic Agents Against Human Leukemic HL-60 Cells," *Life Sciences* 55(13):1061-1069.

* cited by examiner

*Primary Examiner*—Christina Chan
*Assistant Examiner*—Phuong Huynh
(74) *Attorney, Agent, or Firm*—Rothwell, Figg, Ernst & Manbeck, P.C.

(57) ABSTRACT

The invention relates to a method of inhibiting myeloperoxidase activity in neutrophils in an individual by administering to the individual an effective amount of a lignan, where said lignan is enterolactone. The invention is further directed to a method inhibiting myeloperoxidase activity or oxidative burst of macrophages in an individual by administering to the individual an effective amount of a lignan where said lignan is enterolactone or hydroxymatairesinol or a mixture. Finally, the invention is directed to a method of inhibiting oxidative burst or myeloperoxidase activity in neutrophils in an individual by administering to the individual an effective amount of a lignan which is hydroxymatairesinol.

1 Claim, 4 Drawing Sheets

METHOD OF INHIBITING OVERACTIVITY OF PHAGOCYTES OR LYMPHOCYTES IN AN INDIVIDUAL

FIELD OF THE INVENTION

This invention relates to inhibiting the overactivity of phagocytes or lymphocytes in an individual, and to treatment or prevention of diseases and conditions caused by over-activity of said cells.

BACKGROUND OF THE INVENTION

The publications and other materials used herein to illuminate the background of the invention, and in particular, cases to provide additional details respecting the practice, are incorporated by reference.

Medicinal antioxidants are compounds that may be used for the prevention of tissue damage induced by lipid peroxidation (Halliwell, B., *FASEB J* 1:358–364, 1987). During lipid peroxidation free radicals interact with polyunsaturated fatty acids to form lipid peroxyl radicals, which produce lipid hydroperoxides and further lipid peroxyl radicals. This peroxidative cascade may eventually consume an essential part of the membrane lipid, which may lead to changes in membrane permeability and ultimately in cell death. The peroxidative degradation of lipids also leads to the formation of potentially toxic products such as malondialdehyde.

U.S. Pat. No. 5,929,123 discloses the use of halogenated triphenylethylene derivatives for lowering levels of serum lipid peroxides and for treatment or prevention of oxidative tissue damages induced by lipid peroxidation.

Hydroxymatairesinol and matairesinol are both plant lignanes and they have been disclosed to possess various beneficial therapeutical effects.

E. Yesilada et al. (*Cytokine* 13:359–364, 2001) disclose the use of certain compounds, i.e., matairesinol, to decrease tumour necrosis factor alpha (TNF-α) production and the anti-inflammatory activity of the compounds.

The International Patent Application WO 00/59946, assigned to Hormos Nutraceutical Oy Ltd, discloses hydroxymatairesinol as an inhibitor of lipid peroxidation and LDL oxidation, and thus its usefulness as an antioxidant.

The above publications do not, however, disclose the ability of any agent to cause a decrease in the formation of reactive oxygen species which cause the lipid oxidation.

After specific membrane perturbation by either particulate or soluble stimuli, neutrophilic granulocytes (neutrophils) exhibit a burst in oxygen consumption (called the respiratory or oxidative burst). The oxygen consumed is not used in cellular respiration, but is converted primarily to superoxide and hydrogen peroxide. The heme protein myeloperoxidase uses hydrogen peroxide to convert chloride to hypochlorous acid and to convert L-tyrosine to tyrosyl radical. Generation of reactive oxygen species, hypochlorous acid and tyrosyl radical together form the basis of microbicidical action of human neutrophils (FIG. 1). The function of oxidative burst and formation of reactive species have been observed not only in neutrophils, but also in macrophages, microglial cells of the brain, the Kupffer cells of the liver, monocytes, basophils, mast cells, and eosinophils.

Besides the microbicidical action, reactive species generated by the oxidative burst and myeloperoxidase may cause damage to molecules and cellular components of the host organism (FIG. 1). Prolonged overactivity of reactive species generating cell types results in sustained oxidative stress and, hence, tissue damage. Such an overactivity may typically be encountered in a variety of either acute (e.g. ischemia-reperfusion injury in myocardial infarction, stroke and transplantation, and adult respiratory distress syndrome) or chronic (rheumatoid arthritis, asthma, inflammatory bowel disease, HIV, psoriasis and inflammatory conditions of the skin) inflammatory conditions. It is now well known that in addition to the physiological ageing, reactive oxygen species are implicated in the pathophysiology of numerous human diseases.

Attempts to control adverse implications of overactive cellular defence functions have been largely focused on migration, binding and tissue infiltration of these cells. However, since the reactive species produced by oxidative burst and myeloperoxidase are the ultimate damaging agents, it seems logical that a more direct way for attenuation of the damage due to over-activity would be effective inhibition of oxidative burst and myeloperoxidase activity.

Upon allergic and autoimmune reactions and viral infections, lymphocytes (or T-cells) activate and they can act in target tissues by augmenting immune response indirectly by activating other cells such as macrophages and B cells (helper T-cells), or by killing cells infected with viruses directly (cytotoxic T-cells). The recognition of specific antigens by specific T-cell receptors, leads to clonal expansion of specific T-cell population and generation of an adaptive immune response. Autoimmune disease occurs when this adaptive response is initiated against self-antigens.

Extended and persistent autoimmune responses are disadvantageous since they manifest diseases including rheumathoid arthritis and inflammatory bowel disease. They also contribute to allergic reactions and asthma. Therefore, timely termination of this response is essential.

After completion of their mission, T-cells are eliminated through programmed cell death, or apoptosis. An important messenger molecule mediating this self-destruction is a 319 aminoacid transmembrane glycoprotein Fas (also known as Apo 1 or CD95). Fas belongs to tumour necrosis factor receptor superfamily (Itoh et al., *Cell* 66:233–43, 1991). When engaged by its ligand, FasL, it generates a sequential activation of a cascade of intracellular serine proteases, called caspases, leading to destruction of cellular architecture and degradation of DNA by endonucleases.

Resting T-cells express little Fas on the cell surface. After T-cell stimulation (by e.g., T cell receptor), Fas-expression is increased and the T-cells become sensitive to Fas-mediated death (triggered through autocrine and paracrine production of FasL after T cell receptor stimulation). Thus, Fas-FasL system represents an highly important mechanism is regulating T-cell homeostasis.

TNF-α is a pro-inflammatory cytokine that is involved in the pathogenesis of several inflammatory diseases. Blockade of TNF-α has been shown to be useful in the treatment of chronic inflammatory conditions, such as rheumatoid arthritis and Crohn's disease (Flier, J. S. and Underhill, L. H, "The tumor necrosis factor ligand and receptor families", *New Eng. J Med.* 334:1717–1725, 1996).

OBJECT AND SUMMARY OF THE INVENTION

An object of this invention is to decrease the formation of reactive oxygen species, caused by the overactive phagocytes (neutrophils), wherein said reactive oxygen species further could react with lipids, DNA or proteins and thereby cause diseases and disorders in the individual. The object is also to lower the risk, prevent or treat other diseases or conditions, which are not due to lipid, DNA or protein oxidation but which are due to overactive neutrophils.

Another object of the invention is to decrease the TNF-α secretion caused by overactive macrophages and thereby lower the risk, prevent or treat diseases or conditions due to this mechanism.

A further object is to inhibit the overactivity of T-lymphocytes by inducing their self-destroying activity, and thereby lower the risk, prevent or treat diseases or conditions due to this mechanism.

Thus, according to one aspect, this invention relates to a method of inhibiting the overactivity of phagocytes or lymphocytes in an individual by administering to said individual an effective amount of a lignan, wherein said lignan has the formula

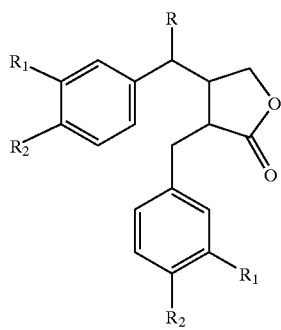

wherein R is H or OH when $R_1$ is $OCH_3$ and $R_2$ is OH or R is H when $R_1$ is OH and $R_2$ is H, wherein said lignan is hydroxymatairesinol when R is OH, $R_1$ is $OCR_3$ and $R_2$ is OH, or is matairesinol when R is H, $R_1$ is $OCH_3$ and $R_2$ is OH or is enterolactone when R is H, $R_1$ is OH and $R_2$ is H, and wherein
i) the phagocytes are neutrophils and the lignan is hydroxymatairesinol or matairesinol or mixtures thereof, or
ii) the phagocytes are cells of myeloid origin and the lignan is enterolactone or hydroxymatairesinol or mixtures thereof, or
iii) the lymphocytes are T-lymphocytes and the lignan is hydroxymatairesinol, matairesinol or enterolactone or mixtures thereof.

According to another aspect, this invention concerns a method of treating or preventing an acute ischemia-reperfusion injury or a chronic condition, caused by overactivty of phagocytes or lymphocytes in an individual, said method comprising decreasing the activity of phagocytes in an indiviual by adminstering to said individual an effective amount of a lignan, wherein
i) the phagocytes are neutrophils and the ligan is hydroxymatairesinol or matairesinol or mixtures thereof, or
ii) the phagocytes are cells of myeloid origin and the ligan is enterolactone or hydroxymatairesinol or mixtures thereof, or
iii) the lymphocytes are T-lymphocytes and the lignan is hydroxymatairesinol, matairesinol or enterolactone or mixtures thereof.

DETAILED DESCRIPTION OF THE INVENTION

Figure 1:
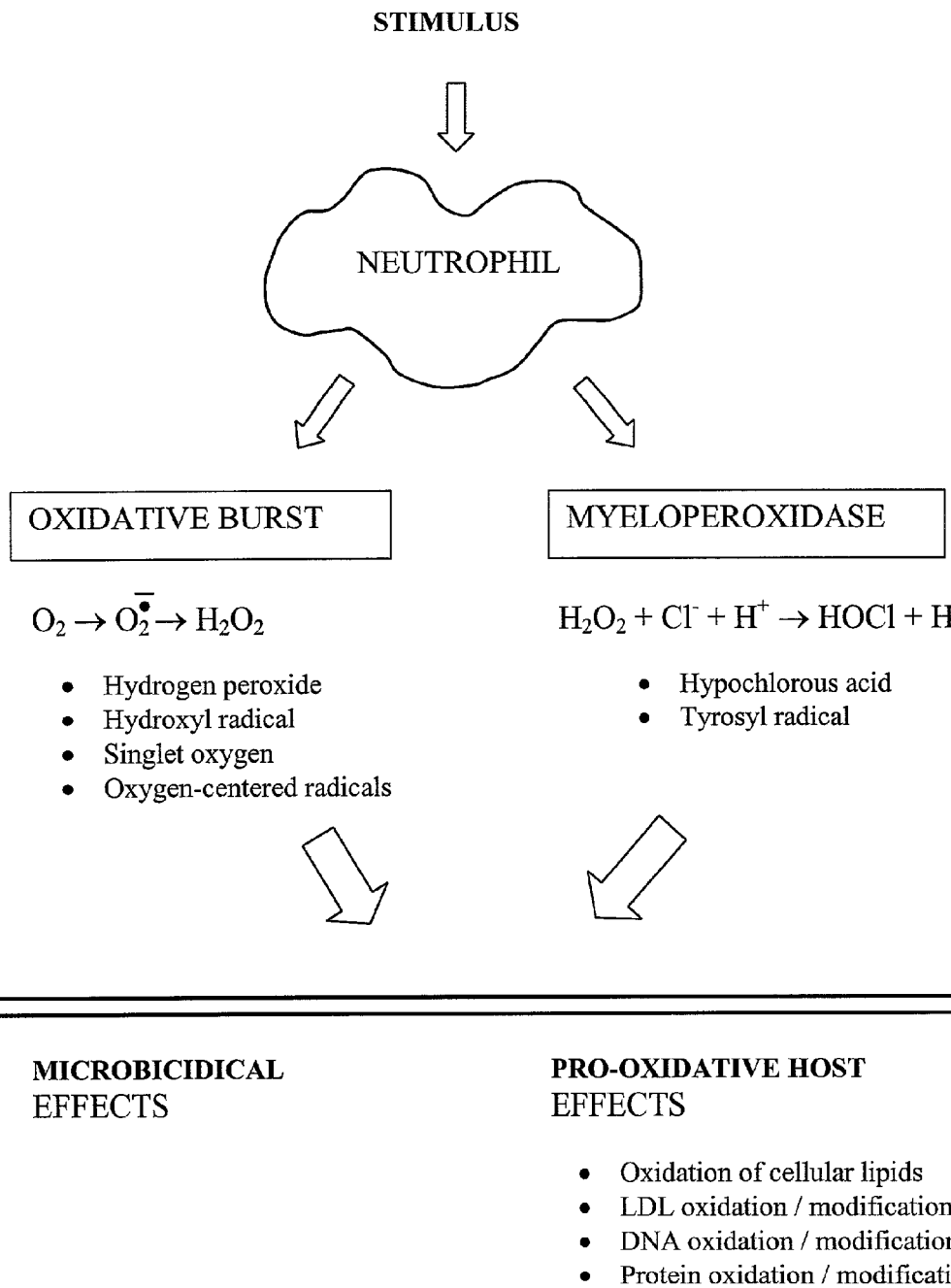
FIG. 1 illustrates the oxidative burst and myeloperoxidase activity as the mechanisms of microbicidial and host pro-oxidative effects of neutrophils.

The wording "hydroxymatairesinol", "matairesinol" or "enterolactone" shall in this text be understood to cover any geometric isomer or stereoisomer or any mixture of isomers, such as racemates, of these compounds. Salts, adducts and complexes of the compounds shall also be understood to be covered by these wordings.

In this text, the wording "inhibiting the overactivity of phagocytes or lymphocytes" shall be understood as decreasing the activity to a level at which the individual's adverse reactions and symptoms are essentially avoided. A certain activity level of phagocyte or lymphocyte activity shall of course be retained so as to ensure their useful biological activity.

The level of the inhibition has been monitored by measuring oxidative burst activity before and during administration of inhibitory substances. Daily administration of carvedilol (6.25 mg for 1 week) decreased reactive oxygen production by neutrophils and mononuclear cells by 59% and 62%, respectively (Dandona, P., Karne, R., Ghanim, H., Hamouda, W., Aljada, A., Magsino, C. H., "Carvedilol inhibitr reactive oxygen species generation by leukocytes and oxidative damage to amino acids", *Circulation* 101: 122–124, 2000). Similarly, alpha-tocopherol supplementation (1200 IU per day for 8 weeks) resulted in 50%–60% decrease in reactive oxygen production by monocytes of healthy volunteers (Devaraj, S., Li, D., Jialal, I., "The effects of alpha tocopherol supplementation on monocyte function. Decreased lipid oxidation, interleukin 1 beta secretion, and monocyte adhesion to endothelium", *J Clin Invest* 98:756–763, 1996).

Normally, the levels of circulating T-lymphocytes are kept within a constant range, ranging from $1-2.5 \times 10^9$/liter of blood. The T-lymphocytes can be further divided in subcategories according to the expression of certain surface antigens (CD4: $0.5-1.6 \times 10^9$/l, CD8: $0.3-0.6 \times 10^9$/L) and their levels can also be estimated. The effect of lignans should be adjusted not to exceed the abovementioned lower limits of circulating lymphocytes.

The term "preventing" a condition or disease caused by overactivity of phagocytes or lymphocytes in an individual shall in the definition of the invention of this invention be understood to include complete prevention as well as lowering said individual's risk of falling ill with said condition or disease.

According to a one preferable embodiment, the oxidative burst caused by stimulus of the neutrophils is decreased and/or the myeloperoxidase activity in converting the reactive oxygen species, released by oxidative burst caused by stimulus of said neutrophils, is decreased.

Conditions which can be treated or prevented by administering hydroxymatairesinol or matairesinol and which conditions result from this mechanism are acute ischemia-reperfusion injuries or chronic conditions.

Such acute ischemia-reperfusion injuries are especially injuries in myocardial infarction, stroke, transplantation, adult respiratory distress syndrome, ischemic heart disease, or endotoxic or hemmorhagic shock.

Typical chronic conditions are rheumatoid arthritis, allergic conditions such as asthma, inflammatory conditions such as inflammatory bowel disease or an inflammatory condition of the skin, HIV, AIDS, psoriasis, Parkinson's disease, Alzheimer's disease, autoimmune diseases, type I or type II diabetes, hypercholesterolemic atherosclerosis, cataract or amylotrophic lateral sclerosis.

According to another embodiment, the activity of T-lymphocytes by inducing their self-destroying activity is decreased.

Conditions which can be treated or prevented by administering hydroxymatairesinol, matairesinol or enterolactone and which conditions result from this mechansim are allergic conditions or autoimmune diseases. As specific diseases can be mentioned rheumathoid arthritis, inflammatory bowel disease, asthma, psoriasis, type I and type II diabetes, type I and type II hypersensitivity reactions, a rejection reaction due to tissue transplantation, atherosclerosis and multiple sclerosis.

According to a third embodiment, the TNF-α-release of cells of myeloid origin is decreased by administering hydroxymatairesinol or enterolactone. Cells of myeloid origin are capable of TNF-α production, and are, for example, monocytes/macrophages, microglial cells or foam cells. Conditions which can be treated or prevented hereby are particularly inflammatory conditions, rheumatoid arthritis, inflammatory bowel disease including also Crohn's disease, Alzheimer's disease, type I or type II diabetes, atherosclerosis, psoriasis or osteoporosis.

The lignans to be used in this invention can be supplied in the form of a pharmaceutical preparation, dietary supplement, clinical nutrition formula or as a functional food.

The pharmaceutical preparation according to this invention is preferably an oral formulation. The required amount of the active compound or mixture of compounds will vary with the compound and the particular condition to be prevented. A typical dose ranges from about 10 to about 2000 mg per day and adult person, preferably 100 to 600 mg per day and adult person. Typical dosage forms include, but are not limited to, oral dosage forms such as powders, granules, capsules, tablets, caplets, lozenges, liquids, elixirs, emulsions and suspensions. All such dosage forms may include conventional carriers, diluents, excipients, binders and additives known to those skilled in the medicinal and pharmaceutical arts.

The pharmaceutical or other formula carriers typically employed may be solid or liquid. Thus, for example, solid carriers include polysaccharides such as lactose, sucrose, gelatin, agar, while liquid carriers include aqueous solutions of salts, polysaccharides, complexing agents, surfactants, syrups, vegetable oils such as peanut oil or olive oil, and certain alcohols. However, any acceptable solid or liquid carrier can be used in the pharmaceutical preparation or other dietary or nutrition formula to be administered according to this invention.

A typical food product, suitable for use in the methods according to this invention, is especially a functional food, a nutritional supplement, a nutrient, a pharmafood, a nutraceutical, a health food, a designer food or any food product. A suitable concentration of the active compound the food product is, for example, 5 to 1000 mg of active compound per 100 g of food product, preferably about 10 to 100 mg of active compound per 100 g of food product.

The invention will be illuminated by the following non-restrictive Examples.

EXAMPLE 1

Effect of Lignans on Oxidative Burst and Myeloperoxidase Activity of Human Neutrophils A. Methods Isolation of neutrophils: Neutrophils were isolated from 30 mL freshly drawn heparinized whole blood, after dextran sedimentation of erythrocytes for 30 min. The leucocyte rich plasma was layered over an equal volume of Percoll (Sigma) and centrifuged at 400×g for 15 min. Erythrocytes, contaminating the neutrophil pellet, were destroyed by osmotic lysis with 0.87% $NH_4Cl$ (pH 7.0). Neutrophils were washed with PBS (pH 7.1) and centrifuged at 200×g for 10 min. Cells were resuspended in fresh HBS (containing 0.8 g NaCl, 0.4 g KCl, 0.06 g $Na_2HPO_4 \times 2\ H_2O$, 0.06 g $KH_2PO_4$, 0.1 g $MgSO_4 \times 7H_2O$ and 1 g glucose in 1000 mL of distilled water; pH adjusted to 7.4 by 7% $NaHCO_3$) and counted before use.

Measurement of neutrophil oxidative burst: Production of reactive oxygen species by neutrophils was recorded by chemiluminescent analysis. Chemiluminescence measurements were performed with Bio-Orbit 1251 Luminometer connected to a personal computer with special programs for the assays (Bio-Orbit, Turku, Finland). The protocol for each assay included automatic pipetting of the appropriate reagent that initiated the reaction in all cuvettes. Six or twelve samples were analyzed simultaneously, depending on the assay. Disposable plastic cuvettes were used throughout.

One millilitre of cell suspension (final cell count $10^6$ cells/mL) was placed in plastic cuvettes, and the level of resting chemiluminescence was recorded before addition of the stimulus; production of reactive oxygen by neutrophils (oxidative burst) was stimulated by addition of phorbol-myristate-acetate (PMA). The buffer (HBS, pH 7.4) was pipetted in a volume of 0.930 mL in the luminometer cuvette. Test compounds were added to incubation mixtures in a small volume (2% of total incubation volume) of ethanol. Ethanol itself did not affect oxidative burst of neutrophils. Fifty microliters of 5 mM lucigenin was added, and the reaction was initiated by 0.020 mL of 0.1 mM PMA at 37° C. The chemiluminescence was measured for about 45 min at 1 min cycles and the area under curve (integral) was calculated. The effects of test compounds were studied at various concentrations in order to demonstrate dose-response of the effect. Based on these experiments, a IC50-value (concentration that under these circumstances produced a 50% inhibition of neutrophil oxidative burst) was determined.

Myeloperoxidase activity: Myeloperoxidase activity was determined by the method of Suzuki et al. (Suzuki, K., Ota, H., Sasagawa, S., Sakatoni, T., Fujikura, T., *Ann Biochem* 132:345–352, 1983) in which the enzyme catalyzes the oxidation of 3,3',5,5'-tetramethylbenzidine by $H_2O_2$ to yield a blue chromogen with a maximum wavelength of 655 nm. Studies on myeloperoxidase inhibition in vitro were performed by adding test compounds to incubation mixtures in a small volume (2% of incubation volume) of ethanol. Ethanol itself did not affect myeloperoxidase activity. The effects of test compounds were studied at various concentrations in order to demonstrate dose-response of the efect. Based on these experiments, a $IC_{50}$-value (concentration that under these circumstances produced a 50% inhibition of myeloperoxidase activity) was determined.

B. Results

The results are shown in Table 1. For comparison, the effects of 4-OH-toremifene, which in earlier studies was found to be a very strong inhibitor of oxidative burst (Ahotupa, M., Kangas, L., "Antioxidant compounds". PCT/FI97/00266; U.S. Pat. No. 5,929,123, 1997) and nitecapone, strongest known myeloperoxidase inhibitor (Vento, A. E., Rämö, O. J., Nemlander, A. T., Ahotupa, M., Nissinen, E., Holopainen, A., Mattila, S. P., *Res Exp Med* 198:299–306, 1999) were tested simultaneously with hydoxymatairesinol and matairesinol.

TABLE 1

The Effects Of Hydroxymatairesinol, Matairesinol, 4-Hydroxy-toremifene And Nitecapone On Oxidative Burst And Myeloperoxidase Activity Of Human Neutrophils In Vitro

| Test compound | Oxidative burst | Myeloperoxidase activity |
|---|---|---|
| Hydroxymatairesinol | 5.3 | 6.8 |
| Matairesinol | 11.0 | 44.5 |
| 4-OH-toremifene | 1.7 | 54.0 |
| Nitecapone | 7.5 | 2.3 |

The results are given as $IC_{50}$-values ($\mu$mol/L).

EXAMPLE 2

Effect of Lignans to Inhibit the Overactivity of T-Lymphocytes by Inducing Their Self-Destroying Activity Increase of Fas-induced apoptosis: The experiment was performed essentially as described in the literature (van Engeland, M., Nieland, L. J. W., Ramaekers, F. C. S., Schutte, B., Reutelingberger, C. P. M., *Cytometry* 31:1–9, 1998).

The human leukemic T cell line, Jurkat (clone EG-1; ATCC, Manassas, Va.), was cultured in RPMI 1640 medium supplemented with 10% inactivated fetal calf serum (FCS), 2 mM L-glutamine, 100 U/ml penicillin, 100 $\mu$g/ml streptomycin in a humidified incubator with 5% C02 in air at 37° C. The cells were kept at a density of $0.5–1.0 \times 10^6$/ml.

The effect of compounds was determined by pre-treating 200 000 Jurkat T-cells with 30 $\mu$M concentration of hydroxymatairesinol, enterolactone and matairesinol for 45 min. To induce apoptosis, 100 ng/ml mouse anti-human CD95 IgM antibody (Kamiya Biomedical Company, Thousand Oaks, Calif.) was added and cells were further incubated for 2 h. Samples were made in duplicates.

To detect phosphatidylserine exposure in apoptotic cells by flow cytometry, Jurkat T cells were washed once with phosphate-buffered saline (PBS) and incubated for 10 min on ice in 400 $\mu$l of binding buffer (2.5 mM HEPES-NaOH pH 7.4, 35 mM NaCl, 0.625 mM $CaCi_2$) with 1 $\mu$l annexin V-FITC (Alexis, Laufelfingen, Switzerland) and analyzed on a FACScan flow cytometer (Becton Dickinson, NJ).

Figure 2:
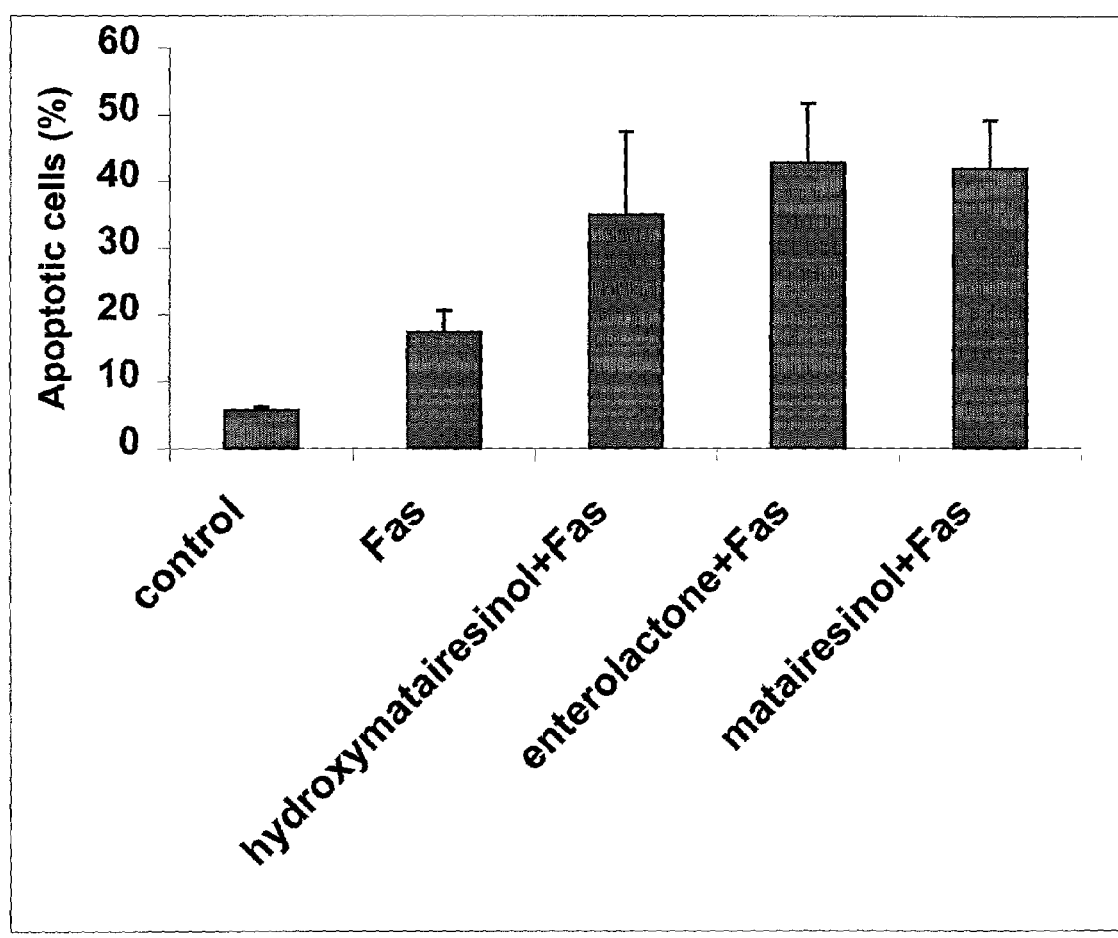
FIG. 2 shows the effect of the tested lignans on the Fas-induced apoptosis in T-cells.

The results are shown in FIG. 2. A 30 $\mu$M concentration of all tested lignans increased Fas-induced apoptosis in Jurkat T-cells from 20% (Fas alone) to 50–60% (combination of hydroxymatairesinol, enterolactone or matairesinol with Fas). The compounds administered alone had no impact on Jurkat cell apoptosis (data not shown).

Effect of lignans on Fas receptor surface (FasR) expression: The experiment was performed essentially as described in the literature (Brunner et al., Nature 373, 441–443, 1995). The surface expression of the FasR was measured by immunostaining alive Jurkat cells with an monoclonal anti-FasR antibody (Medical Biological Laboratories Co. Ltd, Japan, clone CH-11) and an anti-mouse antibody labelled with FITC (Alexis Biochemicals Ltd, USA) according to manufacturers instructions. The fluorescence intensity equals the amount of antibody bound to the FasR on the cell membrane.

Figure 3:
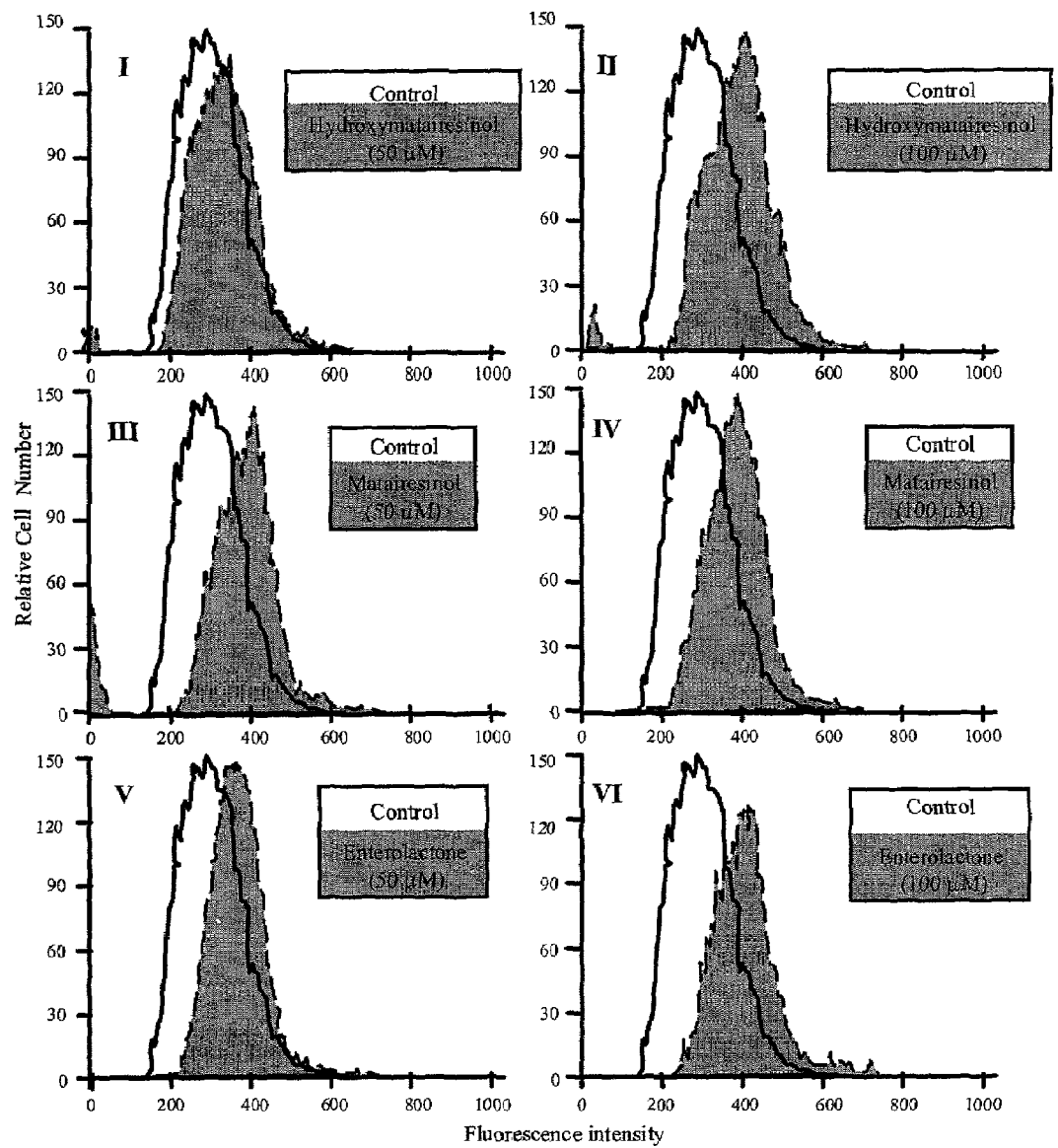
FIG. 3 shows the effect of the tested lignans, for two concentrations, on Fas receptor surface expression.

The results are shown in FIG. 3. Solid line represent distribution on Fas surface expressing control (untreated) Jurkat cells. The distribution shifted to right (gray area, dotted lines) upon treatment with 50 or 100 $\mu$M hydroxymatairesinol, (histogram I and II), enterolactone (III and IV) or matairesinol (V and VI). The shift of the graph to the right indicates cells were immunostained for Fas stronger than the control cells thus expressing elevated level of Fas protein on their plasma membrane.

The findings shown in FIGS. 2 and 3 show that the tested lignans increase cell response to Fas-mediated apoptosis, possibly due to an increase in the plasma membrane Fas expression. Therefore, the tested compounds may be useful for the prevention or treatment autoimmune or allergic diseases.

EXAMPLE 3

Effect of Lignans on LPS-Induced TNF-α Production by Monocytes

Monocytes were isolated from human peripheral blood mononuclear cells by magnetic sorting. The cells were pre-incubated with the lignans matairesinol (as a reference compound) and enterolactone (1–100$\mu$M) or interleukin 10 (IL-10) (100 U/ml) for 24 hours before addition of LPS (1 $\mu$g/ml) into cell culture. After additional 48 hours the levels of TNF- from culture supernatants were measured by ELISA.

Figure 4:
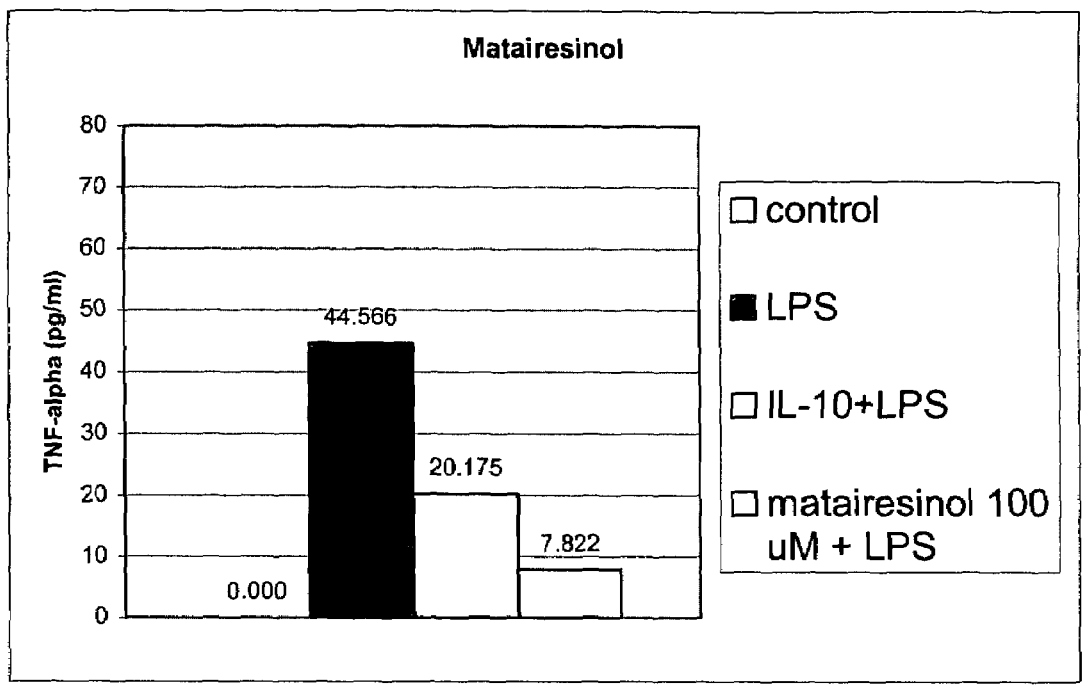
FIGS. 4A and 4B show the effect of matairesinol (FIG. 4A) and enterolactone (FIG. 4B) on the TNF-α secretion of monocytes.
Figure 4:
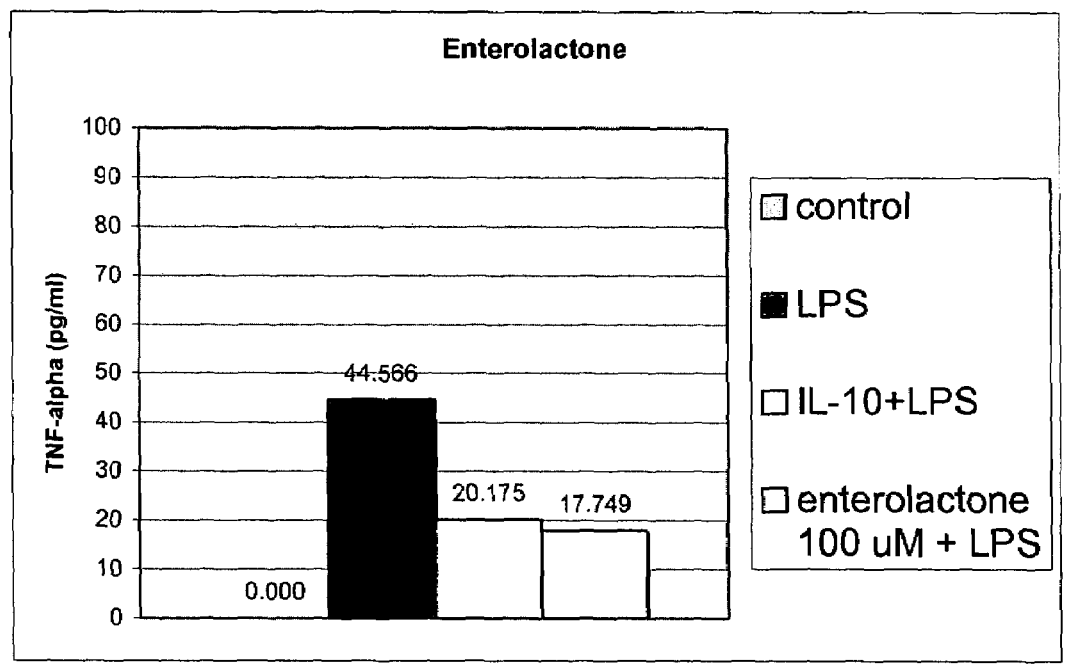

The results are shown in FIGS. 4A and 4B. FIG. 4B shows that matairesinol (as a reference) and enterolactone are at least as effective at concentration of 100 $\mu$M as the positive control, IL-10. Hydroxymatairesinol, although no test results are shown, is also believed to be active in these tests. Therefore, enterolactone and hydroxymatairesinol can be suggested for use as an anti-inflammatory agent inhibiting cytokine production.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

What is claimed is:

1. A method of inhibiting myeloperoxidase activity or oxidative burst in macrophages in an individual by administering to said individual an effective amount of a lignan, wherein said lignan is enterolactone or hydroxymatairesinol or a mixture thereof.

* * * * *